(12) United States Patent
Hastings et al.

(10) Patent No.: US 7,937,161 B2
(45) Date of Patent: May 3, 2011

(54) CARDIAC STIMULATION ELECTRODES, DELIVERY DEVICES, AND IMPLANTATION CONFIGURATIONS

(75) Inventors: Roger N. Hastings, Maple Grove, MN (US); Michael J. Pikus, Golden Valley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1245 days.

(21) Appl. No.: 11/394,601

(22) Filed: Mar. 31, 2006

(65) Prior Publication Data

US 2007/0239248 A1 Oct. 11, 2007

(51) Int. Cl.
*A61N 1/00* (2006.01)
(52) U.S. Cl. ...................................................... 607/127
(58) Field of Classification Search .......... 607/126–127, 607/130–131; 600/375
See application file for complete search history.

(56) References Cited

U.S. PATENT DOCUMENTS

| | | | |
|---|---|---|---|
| 3,057,356 A | 9/1962 | Greatbatch | |
| 3,357,434 A | 12/1967 | Abell | |
| 3,596,662 A | 8/1971 | Bolduc | |
| 3,667,477 A | 6/1972 | Susset et al. | |
| 3,713,449 A | 1/1973 | Mulier | |
| 3,727,616 A | 4/1973 | Lenzkes | |
| 3,835,864 A | 9/1974 | Rasor et al. | |
| 3,943,936 A | 3/1976 | Rasor et al. | |
| 4,010,756 A | 3/1977 | DuMont et al. | |
| 4,162,679 A | 7/1979 | Reenstierna | |
| 4,198,991 A | 4/1980 | Harris | |
| 4,256,115 A | 3/1981 | Bilitch | |
| 4,441,210 A | 4/1984 | Hochmair et al. | |
| 4,524,774 A | 6/1985 | Hildebrandt | |
| 4,641,664 A | 2/1987 | Botvidsson | |
| 4,644,957 A * | 2/1987 | Ricciardelli et al. | 600/376 |
| 4,721,118 A | 1/1988 | Harris | |
| 4,830,006 A | 5/1989 | Haluska et al. | |
| 4,953,564 A | 9/1990 | Berthelsen | |
| 4,987,897 A | 1/1991 | Funke | |
| 5,012,806 A | 5/1991 | De Bellis | |
| 5,078,736 A | 1/1992 | Behl | |
| 5,139,033 A * | 8/1992 | Everett et al. | 607/127 |
| 5,143,090 A | 9/1992 | Dutcher et al. | |

(Continued)

FOREIGN PATENT DOCUMENTS

EP 1 166 820 1/2002

(Continued)

OTHER PUBLICATIONS

"Energy management, wireless and system solutions for highly integrated implantable devices" Doctoral Thesis by Jordi Parramon I Piella for the Universitat Autonoma de Barcelona, certified Dec. 2001.

(Continued)

*Primary Examiner* — Mark W Bockelman
(74) *Attorney, Agent, or Firm* — Schwegman, Lundberg & Woessner, P.A.

(57) ABSTRACT

Some embodiments of an electrode delivery system may be used to deliver a plurality of wired electrodes into one or more chambers of the heart. In particular embodiments, the plurality of wired electrodes may be delivered into a heart chamber through a single guide sheath device. Such a system may be used to deliver one or more wired electrodes to inner wall of the left atrium, the left ventricle, or both.

15 Claims, 7 Drawing Sheets

U.S. PATENT DOCUMENTS

| | | | |
|---|---|---|---|
| 5,170,802 A * | 12/1992 | Mehra | 607/126 |
| 5,178,149 A | 1/1993 | Imburgia et al. | |
| 5,193,539 A | 3/1993 | Schulman et al. | |
| 5,234,437 A | 8/1993 | Sepetka | |
| 5,250,071 A | 10/1993 | Palermo | |
| 5,255,693 A | 10/1993 | Dutcher et al. | |
| 5,261,916 A | 11/1993 | Engelson | |
| 5,300,107 A | 4/1994 | Stokes et al. | |
| 5,304,195 A | 4/1994 | Twyford, Jr. et al. | |
| 5,312,415 A | 5/1994 | Palermo | |
| 5,312,439 A | 5/1994 | Loeb | |
| 5,324,316 A | 6/1994 | Schulman et al. | |
| 5,324,325 A | 6/1994 | Moaddeb | |
| 5,342,408 A | 8/1994 | deCoriolis et al. | |
| 5,350,397 A | 9/1994 | Palermo et al. | |
| 5,383,915 A | 1/1995 | Adams | |
| 5,383,924 A | 1/1995 | Brehier | |
| 5,411,535 A | 5/1995 | Fujii et al. | |
| 5,411,537 A | 5/1995 | Munshi et al. | |
| 5,447,533 A | 9/1995 | Vachon et al. | |
| 5,531,780 A | 7/1996 | Vachon | |
| 5,571,148 A | 11/1996 | Loeb et al. | |
| 5,622,168 A | 4/1997 | Keusch | |
| 5,755,764 A | 5/1998 | Schroeppel | |
| 5,772,693 A | 6/1998 | Brownlee | |
| 5,775,331 A | 7/1998 | Raymond et al. | |
| 5,779,715 A | 7/1998 | Tu | |
| 5,800,535 A | 9/1998 | Howard, III | |
| 5,814,089 A | 9/1998 | Stokes et al. | |
| 5,833,715 A | 11/1998 | Vachon et al. | |
| 5,851,227 A * | 12/1998 | Spehr | 607/126 |
| 5,871,532 A | 2/1999 | Schroeppel | |
| 5,876,429 A | 3/1999 | Schroeppel | |
| 5,876,431 A | 3/1999 | Spehr et al. | |
| 6,053,873 A | 4/2000 | Govari et al. | |
| 6,115,636 A | 9/2000 | Ryan | |
| 6,123,724 A | 9/2000 | Denker | |
| 6,132,456 A * | 10/2000 | Sommer et al. | 607/127 |
| 6,141,588 A | 10/2000 | Cox et al. | |
| 6,141,591 A | 10/2000 | Lenarz et al. | |
| 6,161,029 A | 12/2000 | Spreigl et al. | |
| 6,200,303 B1 | 3/2001 | Verrior et al. | |
| 6,223,079 B1 | 4/2001 | Bakels et al. | |
| 6,240,316 B1 | 5/2001 | Richmond, Jr. et al. | |
| 6,266,567 B1 | 7/2001 | Ishikawa et al. | |
| 6,317,615 B1 | 11/2001 | KenKnight et al. | |
| 6,322,559 B1 | 11/2001 | Daulton et al. | |
| 6,336,937 B1 | 1/2002 | Vonesh et al. | |
| 6,345,202 B2 | 2/2002 | Richmond, Jr. et al. | |
| 6,363,938 B2 | 4/2002 | Saadat et al. | |
| 6,370,434 B1 * | 4/2002 | Zhang et al. | 607/122 |
| 6,381,495 B1 | 4/2002 | Jenkins | |
| 6,385,472 B1 | 5/2002 | Hall et al. | |
| 6,409,674 B1 | 6/2002 | Brockway et al. | |
| 6,442,413 B1 | 8/2002 | Silver | |
| 6,445,953 B1 | 9/2002 | Bulkes et al. | |
| 6,456,256 B1 | 9/2002 | Amundson et al. | |
| 6,510,345 B1 | 1/2003 | Van et al. | |
| 6,522,926 B1 | 2/2003 | Kieval et al. | |
| 6,556,874 B2 | 4/2003 | Audoglio | |
| 6,571,127 B1 | 5/2003 | Ben-Haim et al. | |
| 6,582,441 B1 | 6/2003 | He et al. | |
| 6,589,230 B2 | 7/2003 | Gia et al. | |
| 6,614,406 B2 | 9/2003 | Amundson et al. | |
| 6,647,291 B1 | 11/2003 | Bonner et al. | |
| 6,647,292 B1 | 11/2003 | Bardy et al. | |
| 6,783,499 B2 | 8/2004 | Schwartz | |
| 6,895,265 B2 | 5/2005 | Silver | |
| 6,895,280 B2 | 5/2005 | Meadows et al. | |
| 6,901,294 B1 | 5/2005 | Whitehurst et al. | |
| 6,907,285 B2 | 6/2005 | Denker et al. | |
| 6,947,792 B2 | 9/2005 | Ben-Haim et al. | |
| 6,970,742 B2 | 11/2005 | Mann et al. | |
| 6,978,173 B2 | 12/2005 | Stoll et al. | |
| 7,003,350 B2 | 2/2006 | Denker et al. | |
| 7,076,305 B2 | 7/2006 | Imran et al. | |
| 7,231,260 B2 | 6/2007 | Wallace et al. | |
| 2001/0018547 A1 | 8/2001 | Mechlenburg et al. | |
| 2002/0026228 A1 | 2/2002 | Schauerte | |
| 2002/0065543 A1 | 5/2002 | Gomperz et al. | |
| 2002/0077556 A1 | 6/2002 | Schwartz | |
| 2002/0077685 A1 | 6/2002 | Sundquist et al. | |
| 2002/0123785 A1 * | 9/2002 | Zhang et al. | 607/126 |
| 2002/0128546 A1 | 9/2002 | Silver | |
| 2002/0138100 A1 | 9/2002 | Stoll et al. | |
| 2002/0183791 A1 | 12/2002 | Denker et al. | |
| 2002/0188323 A1 | 12/2002 | Penner et al. | |
| 2002/0198604 A1 | 12/2002 | Schulman et al. | |
| 2003/0036773 A1 | 2/2003 | Whitehurst et al. | |
| 2003/0050681 A1 | 3/2003 | Pianca et al. | |
| 2003/0055465 A1 | 3/2003 | Ben-Haim et al. | |
| 2003/0055466 A1 | 3/2003 | Ben-Haim et al. | |
| 2003/0055467 A1 | 3/2003 | Ben-Haim et al. | |
| 2003/0109914 A1 | 6/2003 | Westlund et al. | |
| 2003/0114735 A1 | 6/2003 | Silver et al. | |
| 2003/0114742 A1 | 6/2003 | Lewkowicz et al. | |
| 2003/0158584 A1 | 8/2003 | Cates et al. | |
| 2003/0181958 A1 | 9/2003 | Dobak, III | |
| 2003/0181959 A1 | 9/2003 | Dobak, III | |
| 2003/0204206 A1 | 10/2003 | Padua et al. | |
| 2003/0216729 A1 | 11/2003 | Marchitto et al. | |
| 2003/0236518 A1 | 12/2003 | Marchitto et al. | |
| 2004/0019364 A1 | 1/2004 | Kieval et al. | |
| 2004/0059280 A1 | 3/2004 | Makower et al. | |
| 2004/0059392 A1 | 3/2004 | Parramon et al. | |
| 2004/0073267 A1 | 4/2004 | Holzer | |
| 2004/0087831 A1 | 5/2004 | Michels et al. | |
| 2004/0097805 A1 | 5/2004 | Verard et al. | |
| 2004/0098068 A1 | 5/2004 | Carbunaru et al. | |
| 2004/0106954 A1 | 6/2004 | Whitehurst et al. | |
| 2004/0127895 A1 | 7/2004 | Flock et al. | |
| 2004/0147969 A1 | 7/2004 | Mann et al. | |
| 2004/0147973 A1 | 7/2004 | Hauser et al. | |
| 2004/0167580 A1 | 8/2004 | Mann et al. | |
| 2004/0171355 A1 | 9/2004 | Yu et al. | |
| 2004/0172083 A1 | 9/2004 | Penner | |
| 2004/0176672 A1 | 9/2004 | Silver et al. | |
| 2004/0176822 A1 | 9/2004 | Thompson et al. | |
| 2004/0193092 A1 | 9/2004 | Deal | |
| 2004/0193229 A1 | 9/2004 | Starkebaum et al. | |
| 2004/0210282 A1 | 10/2004 | Flock et al. | |
| 2004/0215092 A1 | 10/2004 | Fischell et al. | |
| 2004/0230090 A1 | 11/2004 | Hegde et al. | |
| 2004/0230255 A1 | 11/2004 | Dobak, III | |
| 2005/0021108 A1 | 1/2005 | Klosterman et al. | |
| 2005/0043765 A1 | 2/2005 | Williams et al. | |
| 2005/0051243 A1 | 3/2005 | Forbes Jones et al. | |
| 2005/0057905 A1 | 3/2005 | He et al. | |
| 2005/0065575 A1 | 3/2005 | Dobak | |
| 2005/0080346 A1 | 4/2005 | Gianchandani et al. | |
| 2005/0080459 A1 | 4/2005 | Jacobson et al. | |
| 2005/0095197 A1 | 5/2005 | Tuszynski et al. | |
| 2005/0096702 A1 | 5/2005 | Denker et al. | |
| 2005/0131511 A1 | 6/2005 | Westlund | |
| 2005/0136385 A1 | 6/2005 | Mann | |
| 2005/0165456 A1 | 7/2005 | Mann | |
| 2005/0182456 A1 | 8/2005 | Ziobro et al. | |
| 2005/0182465 A1 | 8/2005 | Ness | |
| 2005/0192637 A1 | 9/2005 | Girouard et al. | |
| 2005/0215764 A1 | 9/2005 | Tuszynski et al. | |
| 2005/0245846 A1 | 11/2005 | Casey | |
| 2005/0249667 A1 | 11/2005 | Tuszynski et al. | |
| 2005/0251238 A1 | 11/2005 | Wallace et al. | |
| 2005/0251240 A1 | 11/2005 | Doan | |
| 2005/0256549 A1 | 11/2005 | Holzer | |
| 2005/0261741 A1 | 11/2005 | Libbus et al. | |
| 2005/0273014 A1 | 12/2005 | Gianchandani et al. | |
| 2005/0288727 A1 | 12/2005 | Penner | |
| 2006/0015097 A1 | 1/2006 | Mulier et al. | |
| 2006/0020316 A1 | 1/2006 | Martinez et al. | |
| 2006/0085039 A1 | 4/2006 | Hastings et al. | |
| 2006/0085041 A1 | 4/2006 | Hastings et al. | |
| 2006/0085042 A1 | 4/2006 | Hastings et al. | |
| 2006/0095089 A1 | 5/2006 | Soykan et al. | |
| 2006/0136001 A1 | 6/2006 | Ortega et al. | |
| 2006/0136004 A1 | 6/2006 | Cowan et al. | |
| 2007/0075905 A1 | 4/2007 | Denker et al. | |

| | | | |
|---|---|---|---|
| 2007/0106357 A1 | 5/2007 | Denker et al. | |
| 2007/0150009 A1 | 6/2007 | Kveen et al. | |
| 2007/0203556 A1 | 8/2007 | Rutten et al. | |
| 2008/0021532 A1 | 1/2008 | Kveen et al. | |
| 2008/0039904 A1 | 2/2008 | Bulkes et al. | |
| 2008/0046040 A1 | 2/2008 | Denker et al. | |
| 2008/0077184 A1 | 3/2008 | Denker et al. | |
| 2008/0077188 A1 | 3/2008 | Denker et al. | |
| 2008/0119911 A1 | 5/2008 | Rosero | |
| 2009/0204170 A1 | 8/2009 | Hastings et al. | |

FOREIGN PATENT DOCUMENTS

| | | | |
|---|---|---|---|
| EP | 1166820 A2 * | 1/2002 | |
| EP | 1166832 A1 * | 1/2002 | |
| EP | 1166832 A2 | 1/2002 | |
| EP | 1264572 A1 | 12/2002 | |
| EP | 0904009 B1 | 9/2003 | |
| FR | 2559391 | 8/1985 | |
| JP | 05-076501 | 3/1993 | |
| NZ | 526115 | 10/2006 | |
| NZ | 539770 | 10/2007 | |
| NZ | 539771 | 10/2007 | |
| WO | WO-91/16864 A1 | 11/1991 | |
| WO | WO-96/39932 A1 | 12/1996 | |
| WO | WO-97/45157 A1 | 12/1997 | |
| WO | WO-98/26840 A1 | 6/1998 | |
| WO | WO-98/29030 A1 | 7/1998 | |
| WO | WO-98/57592 A1 | 12/1998 | |
| WO | WO-99/03533 A1 | 1/1999 | |
| WO | 99/06102 * | 2/1999 | |
| WO | WO 99/06102 | 2/1999 | |
| WO | WO-99/06102 A1 | 2/1999 | |
| WO | WO-01/00114 A1 | 1/2001 | |
| WO | WO-01/87137 A2 | 11/2001 | |
| WO | WO 03/053491 | 7/2003 | |
| WO | WO-03/053491 A2 | 7/2003 | |
| WO | WO-03/076010 A1 | 9/2003 | |
| WO | WO-03/082403 A2 | 10/2003 | |
| WO | WO-03/096918 A1 | 11/2003 | |
| WO | WO-03/099102 A2 | 12/2003 | |
| WO | WO-2004/002572 A1 | 1/2004 | |
| WO | WO-2004/032788 A2 | 4/2004 | |
| WO | WO-2004/078025 A2 | 9/2004 | |
| WO | WO-2005/058143 A2 | 6/2005 | |
| WO | WO-2005/096954 A2 | 10/2005 | |
| WO | WO-2005/101660 A1 | 10/2005 | |
| WO | WO-2005/107852 A1 | 11/2005 | |
| WO | WO-2005/107863 A2 | 11/2005 | |
| WO | WO-2005/117737 A2 | 12/2005 | |
| WO | WO 2006/045075 | 4/2006 | |
| WO | WO-2006/096685 A1 | 9/2006 | |
| WO | WO-2007/115044 A2 | 10/2007 | |
| WO | WO-2009/099597 A1 | 8/2009 | |

OTHER PUBLICATIONS

"Breakthrough Products Could Put Lesser-Known Firms on the Map", by E. Swain, *MDEA 2004*, pp. 56-58, Apr. 2004.

"Novel Passive Implantable Atrial Defibrillator Using Transcutaneous Radiofrequency Energy Transmission Successfully Cardioverts Atrial Fibrillation" by Manoharan et al., for *Circulation*, pp. 1382-1388, Sep. 16, 2003.

Wagner, "Electrodes, Leads, and Biocompatibility," *Design of Cardiac Pacemakers*, 1993, Chapter 6, pp. 133-160 and TOC.

"U.S. Appl. No. 11/490,576, Non-Final Office Action mailed Oct. 5, 2009", 8 pgs.

"U.S. Appl. No. 11/490,916, Response filed Sep. 3, 2009 to Non Final Office Action mailed May 5, 2009", 13 pgs.

"U.S. Appl. No. 11/511,152, Response filed Nov. 12, 2009 to Final Office Action mailed Aug. 10, 2009", 13 pgs.

"U.S. Appl. No. 11/549,352, Appeal Brief filed Sep. 9, 2009", 36 pgs.

"U.S. Appl. No. 11/683,577, Final Office Action mailed Nov. 9, 2009", 14 pgs.

"U.S. Appl. No. 11/745,105, Non-Final Office Action mailed Sep. 18, 2009", 9 pgs.

"U.S. Appl. No. 11/316,120, Final Office Action mailed Nov. 12, 2009", 8 pgs.

"U.S. Appl. No. 10/971,550, Amendment Under 37 C.F.R. § 1.312 filed Mar. 20, 2009", 6 pgs.

"U.S. Appl. No. 11/075,375, Response filed Jul. 16, 2009 to Final Office Actin mailed Apr. 16, 2009", 13 pgs.

"U.S. Appl. No. 11/075,376, Response filed Jun. 9, 2008 to Final Office Action mailed Jan. 7, 2008", 20 pgs.

"U.S. Appl. No. 11/075,376, Non-Final Office Action Mailed Aug. 20, 2008", 15 pgs.

"U.S. Appl. No. 11/075,376, Response filed May 7, 2007 to Restriction Requirement mailed Apr. 10, 2007", 10 pgs.

"U.S. Appl. No. 11/075,376, Final Office Action mailed Jan. 7, 2008", 11 pgs.

"U.S. Appl. No. 11/075,376, Non-Final Office Action mailed Jun. 26, 2007", 9 pgs.

"U.S. Appl. No. 11/075,376, Response filed Jan. 21, 2009 to Non-Final Office Action mailed Aug. 20, 2008", 22 pgs.

"U.S. Appl. No. 11/075,376, Response filed Oct. 26, 2007 to Non-Final Office Action mailed Jun. 26,2007", 14 pgs.

"U.S. Appl. No. 11/075,376, Restriction Requirement mailed Apr. 10, 2007", 6 pgs.

"U.S. Appl. No. 11/075,376, Final Office Action mailed Apr. 8, 2009", 17 pgs.

"U.S. Appl. No. 11/075,376, Notice of Allowance mailed Aug. 24, 2009", 6 pgs.

"U.S. Appl. No. 11/075,376, Response filed Jul. 8, 2009 to Final Office Action mailed Apr. 8, 2009", 11 pgs.

"U.S. Appl. No. 11/316,120, Final Office Action mailed Aug. 20, 2008", 8 pgs.

"U.S. Appl. No. 11/316,120, Response filed Dec. 22, 2008 to Final Office Action mailed Aug. 20, 2008", 13 pgs.

"U.S. Appl. No. 11/316,120, Non-Final Office Action mailed Apr. 17, 2009", 8 pgs.

"U.S. Appl. No. 11/316,120, Response filed Jul. 17, 2009 to Non Final Office Action mailed Apr. 17, 2009", 13 pgs.

"U.S. Appl. No. 11/490,576, Non Final Office Action mailed on Jul. 9, 2008", 15 pgs.

"U.S. Appl. No. 11/490,576, Response filed Nov. 10, 2008 to Non-Final Office Action mailed Jul. 9, 2008", 20 pgs.

"U.S. Appl. No. 11/490,576, Non-Final Office Action mailed Feb. 17, 2009", 8 pgs.

"U.S. Appl. No. 11/490,576, Response filed Jun. 17, 2009 to Non Final Office Action mailed Feb. 17, 2009", 13 pgs.

"U.S. Appl. No. 11/490,916, Restriction Requirement mailed Dec. 11, 2008", 8 pgs.

"U.S. Appl. No. 11/490,916, Non Final Office Action mailed May 5, 2009", 10 pgs.

"U.S. Appl. No. 11/511,152, Final Office Action mailed Aug. 10, 2009", 13 pgs.

"U.S. Appl. No. 11/549,352, Non-Final Office Action mailed Feb. 5, 2008", 11 pgs.

"U.S. Appl. No. 11/549,352, Final Office Action mailed Mar. 9, 2009", 10 pgs.

"U.S. Appl. No. 11/549,352, Notice of Panel Decision from Pre-Appeal Brief Review mailed Feb. 2, 2009", 2 pgs.

"U.S. Appl. No. 11/549,352, Pre-Appeal Brief for Review filed Dec. 20, 2008", 5 pgs.

"U.S. Appl. No. 11/549,352, Response filed Jul. 7, 2008 to Non-Final Office Action mailed Feb. 5, 2008", 17 pgs.

"U.S. Appl. No. 11/549,352, Final Office Action mailed Aug. 26, 2008", 13 pgs.

"U.S. Appl. No. 11/683,577, Non-Final Office Action mailed Mar. 5, 2009", 13 pgs.

"U.S. Appl. No. 11/683,577, Response filed Aug. 5, 2009 to Non Final Office Action mailed Mar. 5, 2009", 10 pgs.

"U.S. Appl. No. 11/683,584, Non-Final Office Action mailed Apr. 1, 2009", 9 pgs.

"U.S. Appl. No. 11/683,584, Response filed Jul. 1, 2009 to Non Final Office Action mailed Apr. 1, 2009", 7 pgs.

"U.S. Appl. No. 11/745,070, Non Final Office Action mailed Apr. 27, 2009", 11 pgs.

"U.S. Appl. No. 11/745,070, Response filed Jul. 27, 2009 to Non Final Office Action mailed Apr. 27, 2009", 11 pgs.

"European Application Serial No. 06825988.6, Office Action mailed Mar. 4, 2009", 7 pgs.

"European Application Serial No. 07759589.0, Office Action Mailed Jan. 29, 2009", 3 pgs.

"European Application Serial No. 07759589.0, Response filed Jun. 5, 2009 to Office Action mailed Jan. 29, 2009", 6 pgs.

"International Application Serial No. PCT/US2006/040291, International Search Report mailed Apr. 4, 2007", 5 pgs.

"International Application Serial No. PCT/US2006/040291 Written Opinion mailed Apr. 4, 2007", 9 pgs.

"International Application Serial No. PCT/US2005/037978, International Search Report mailed Jun. 13, 2006", 5 pgs.

"International Application Serial No. PCT/US2005/037978, Written Opinion mailed Jun. 13, 2006", 12 pgs.

"International Application Serial No. PCT/US2005/037979, International Search Report mailed Mar. 21, 2006", 4 pgs.

"International Application Serial No. PCT/US2005/037979, Written Opinion mailed Mar. 21, 2006", 8 pgs.

"International Application Serial No. PCT/US2007/078405, International Search Report mailed May 20, 2008", 5 pgs.

"International Application Serial No. PCT/US2007/078405, Written Opinion mailed May 20, 2008", 7 pgs.

"International Application Serial No. PCT/US2009/000693, International Search Report mailed May 8, 2009", 5 pgs.

"International Application Serial No. PCT/US2009/000693, Written Opinion mailed May 8, 2009", 8 pgs.

"International Application Serial No. PCT/US2007/074135, International Search Report mailed Nov. 6, 2007", 4 pgs.

"International Application No. PCT/US2007/074135, Written Opinion mailed Nov. 6, 2007", 8 pgs.

"Telemetry Research Transcutaneous Energy Transfer (TET) Technology Summary", *Telemetry Research Ltd.*, www.telemetryresearch.com, (No date listed), 1 pg.

* cited by examiner

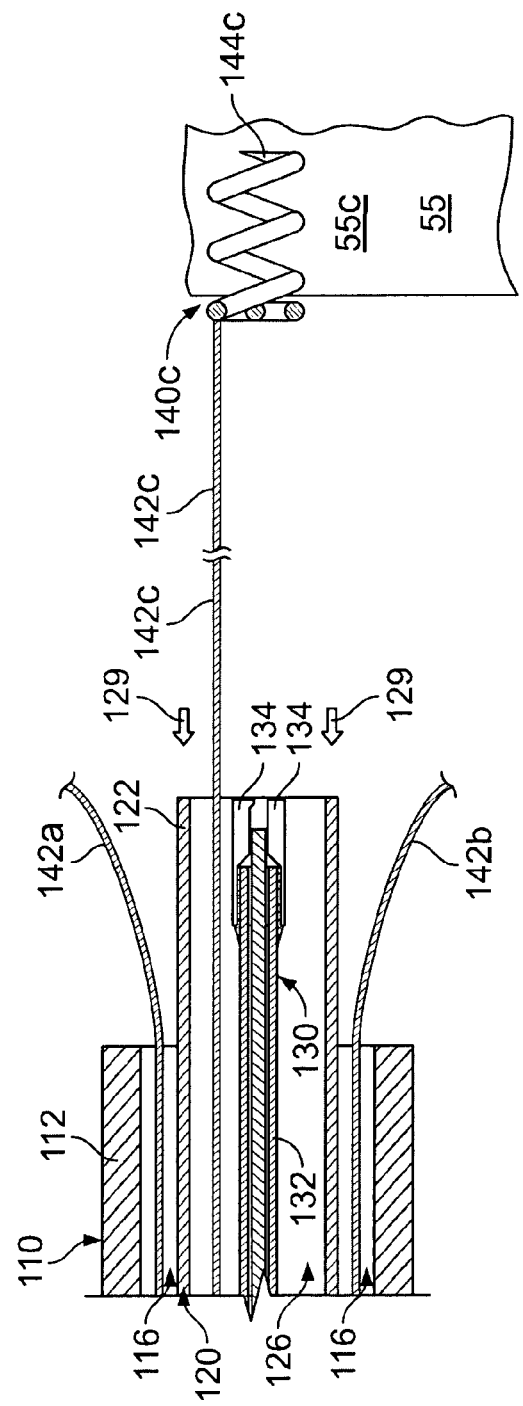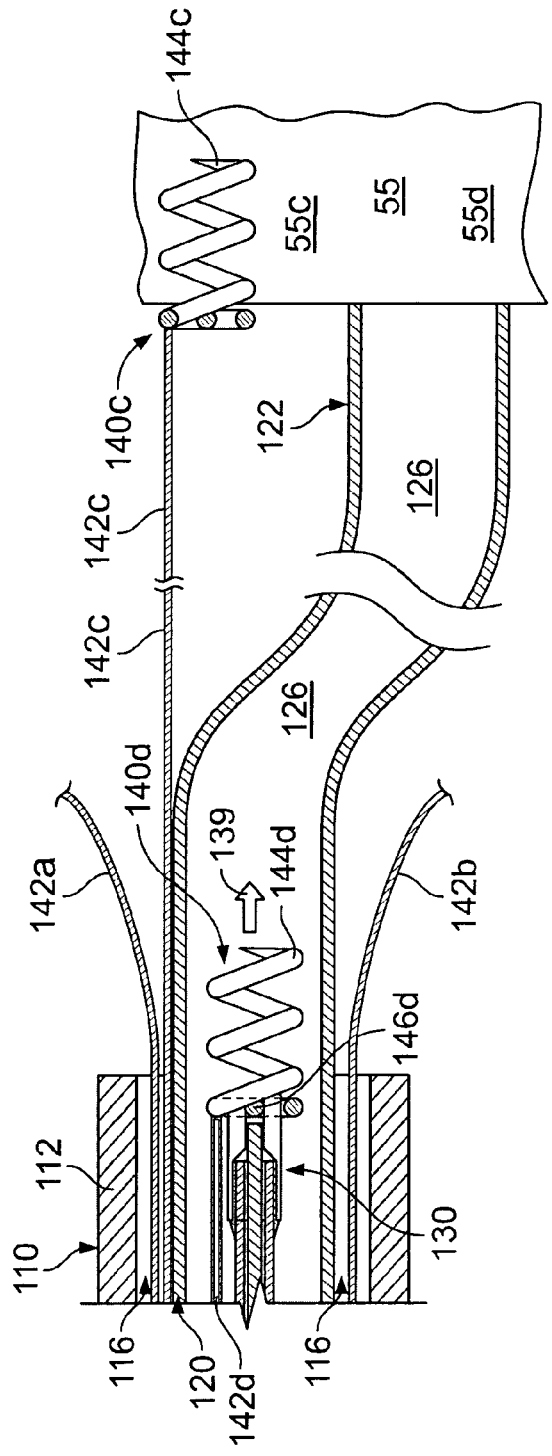
FIG. 4A
FIG. 4B

CARDIAC STIMULATION ELECTRODES, DELIVERY DEVICES, AND IMPLANTATION CONFIGURATIONS

TECHNICAL FIELD

This documents relates to inserting electrodes into one or more chambers of a heart.

BACKGROUND

Pacing instruments can be used to treat patients suffering from any of a number of heart conditions, such as a reduced ability to deliver sufficient amounts of blood from the heart. For example, some heart conditions may cause or be caused by conduction defects in the heart. These conductions effects may lead to irregular or ineffective heart contractions. Some pacing instruments (e.g., a pacemaker) may be implanted in a patient's body so that pacing electrodes in contact with the heart tissue provide electrical stimulation to regulate electrical conduction in the heart tissue. Such regulated electrical stimulation may cause the heart to contract and hence pump blood.

Pacemakers may include a pulse generator that is implanted, typically in a patient's pectoral region just under the skin. One or more wired leads extend from the pulse generator so as to contact various portions of the heart. An electrode at a distal end of a lead may provide the electrical contact to the heart for delivery of the electrical pulses generated by the pulse generator and delivered to the electrode through the lead.

The use of wired leads may limit the number of sites of heart tissue at which electrical energy may be delivered. For example, most commercially available pacing leads are not indicated for use inside the left chambers of the heart. One reason is that the high pumping pressure in the left chambers of the heart may cause a thrombus or clot that forms on the bulky wired lead to eject into distal arteries, thereby causing stroke or other embolic injury. Thus, in order to pace the left side of the heart with a wired lead, most wired leads are directed through the cardiac venous system (outside the left chambers of the heart) to a site in a cardiac vein along the exterior of the left side of the heart. In one example, a treatment known as biventricular pacing may be performed when the walls of the left ventricle are unable to contract at the same time as the walls of the right ventricle. In general, a first wired lead is implanted through a vein into the right atrium, a second wired lead is implanted through a vein into the right ventricle, and a third wired lead is implanted through a vein and into the coronary sinus vein (to pace the left ventricle wall from outside the left ventricle). These three wired leads may be connected to a pacemaker device in an attempt to regulate the contractions of the right and left ventricles. Typically, no wired leads are implanted inside the left chambers of the heart. Further, the number of wired leads to pace the left side of the heart may be limited because multiple leads positioned in cardiac veins can cause significant occlusion.

SUMMARY

Some embodiments of an electrode delivery system may be used to deliver a plurality of wired electrodes to one or more chambers of the heart. In these circumstances, the plurality of wired electrodes may be delivered into a heart chamber through a single guide sheath device. Thus, multiple pacing sites may be established within one or more heart chambers in an efficient manner, without the need to deliver each of the wired electrodes through its own separate outer guide sheath. In certain embodiments, such a system may be used to deliver one or more wired electrodes to inner wall of the left atrium, the left ventricle, or both (rather than the delivery through a cardiac vein to a site along the exterior of the left atrium or left ventricle). In particular embodiments, a plurality of wireless electrode assemblies may be delivered to one or more heart chambers to serve as pacing electrodes in addition to the wired electrodes implanted in the heart chambers.

In some embodiments, a cardiac stimulation wired electrode assembly may include a fixation device to be driven in a direction of a longitudinal axis of the fixation device to implant the fixation device in a wall of a body heart chamber. The fixation device may comprise a conductive material. The assembly may also include at least one insulated wire having an outside diameter of less than about 0.010 inches. The wire may be electrically connected to the conductive material of the fixation device so that electrical pulses are deliverable through the fixation device and to at least a portion of the heart tissue.

In certain embodiments, a cardiac stimulation wired electrode assembly may include a fixation device to be driven in a direction of a longitudinal axis of the fixation device to implant the fixation device in a wall of a body heart chamber. The fixation device may comprise a conductive material. The assembly may also include at least one insulated wire having a first end that is attached to the fixation device at an attachment point that is laterally offset from the longitudinal axis of the fixation device. The at least one insulated wire may also have a second end that is connectable to an implantable pulse generator device.

In some embodiments, a system for inserting cardiac stimulation electrodes into one or more heart chambers may include a guide sheath device having a distal end and a guide conduit extending therethrough. The system may also include an inner sheath device having a distal end to pass through the guide conduit and having an inner conduit extending therethrough. The system may further include a deployment device to direct one or more wired electrodes through the inner conduit into a heart chamber. The inner sheath device may have a lateral width smaller than the guide conduit such that the inner sheath device is slidable through the guide conduit to direct a second electrode toward a second tissue site in the heart chamber while a wire of a first electrode previously delivered to a first tissue site is disposed in the guide conduit laterally outside the inner sheath device.

Some embodiments may include a method of inserting cardiac stimulation electrodes into one or more heart chambers. The method may include directing a distal end of an elongate member to a position at least partially in a heart chamber. The elongate member may have a conduit extending therethrough to the distal end. The method may also include directing a distal portion of a first wired electrode through the conduit of the elongate member and into the heart chamber. The method may further include securing at least a portion of the first wired electrode to a first tissue site in the heart chamber. The method may also include directing a distal portion of a second wired electrode through the conduit of the elongate member and into the heart chamber while a wire of the first wired electrode is disposed in the elongate member conduit adjacent to a wire of the second wired electrode.

These and other embodiments may provide one or more of the following advantages. First, the electrode delivery system may be used to deliver a plurality of wired electrodes through a single lumen for attachment to the inner wall of at least one heart chamber. Second, the wired electrodes or wireless electrode assemblies delivered by the system can create multiple pacing sites or other electrical stimulation sites inside the heart chambers, which may provide consistent pacing stimulation, effective defibrillation, and treatment for a number of heart conditions. Third, the multiple pacing sites or electrical stimulation sites may be established within one or more heart chambers in an efficient manner. Fourth, an inner sheath device may be navigated in the one or more heart chambers without substantial restriction from the wires of the previously implanted electrodes. Fifth, the electrode delivery system may be used to deliver one or more wired electrodes to inner wall of the left atrium, the left ventricle, or both, thereby reducing the need to deliver wired leads through a cardiac vein to a site along the exterior of the left atrium or left ventricle. Sixth, the outer sheath device may permit a plurality of wired electrodes or wireless electrode assemblies to be delivered inside the left heart chambers (e.g., the left atrium and the left ventricle) without harming or damaging the atrial septum from multiple device crossings through the fossa ovalis.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4A-B are partial cross-section views of a portion of an electrode delivery system, in accordance with some embodiments described herein.

Like reference symbols in the various drawings indicate like elements.

DETAILED DESCRIPTION OF ILLUSTRATIVE EMBODIMENTS

Some embodiments of an electrode delivery system may be used to deliver a plurality of wired electrodes through a single guide sheath device into one or more chambers of the heart. Thus, multiple pacing sites may be established within one or more heart chambers in an efficient manner. In certain embodiments, such a system may be used to deliver one or more wired electrodes to an inner wall of the left atrium, the left ventricle, or both (rather than the delivery through a cardiac vein to a site outside of the left atrium or left ventricle).

Figure 1:
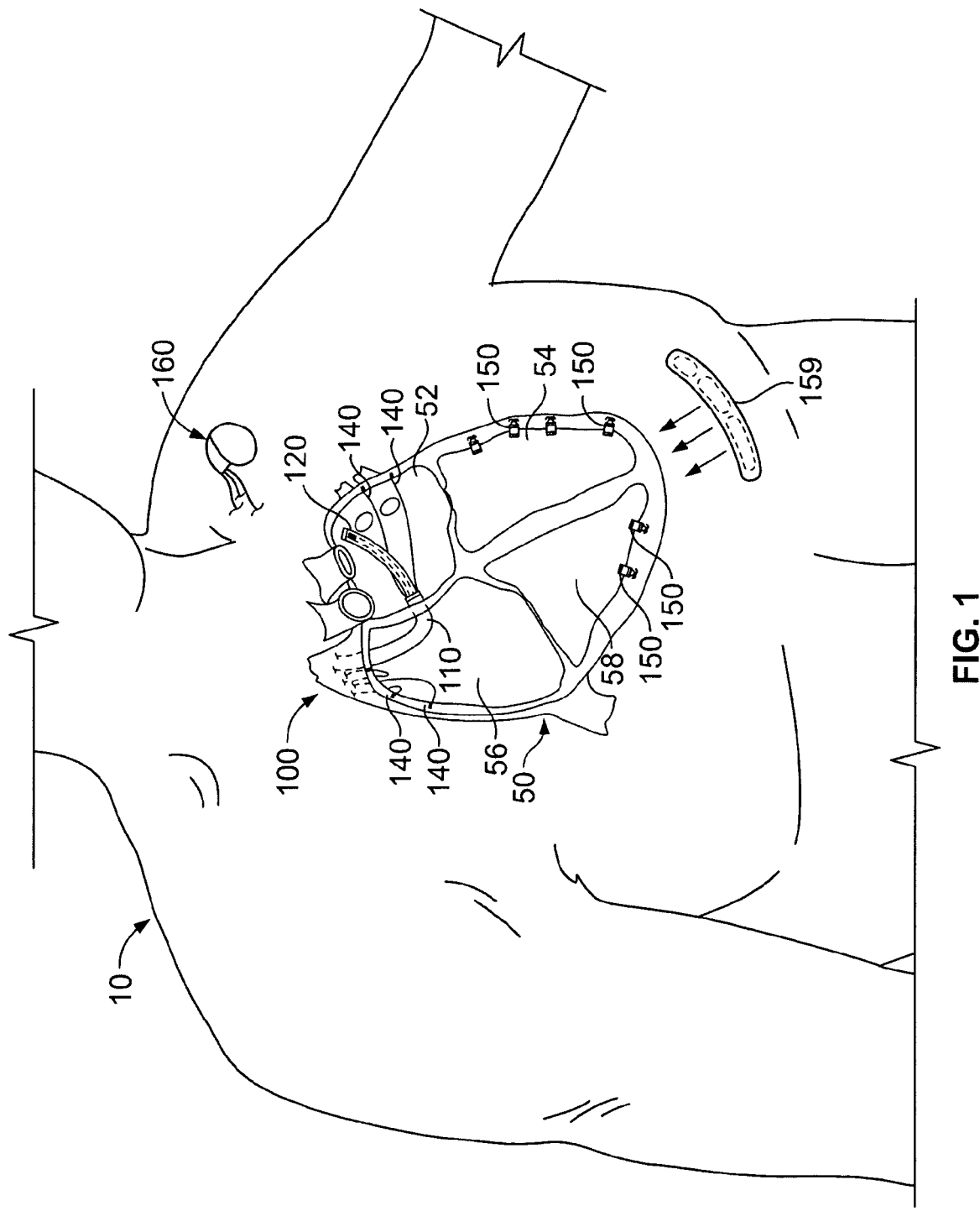
FIG. 1 is a perspective view of a pulse generator and of electrodes in a plurality of heart chambers, in accordance with some embodiments described herein.
Figure 2:
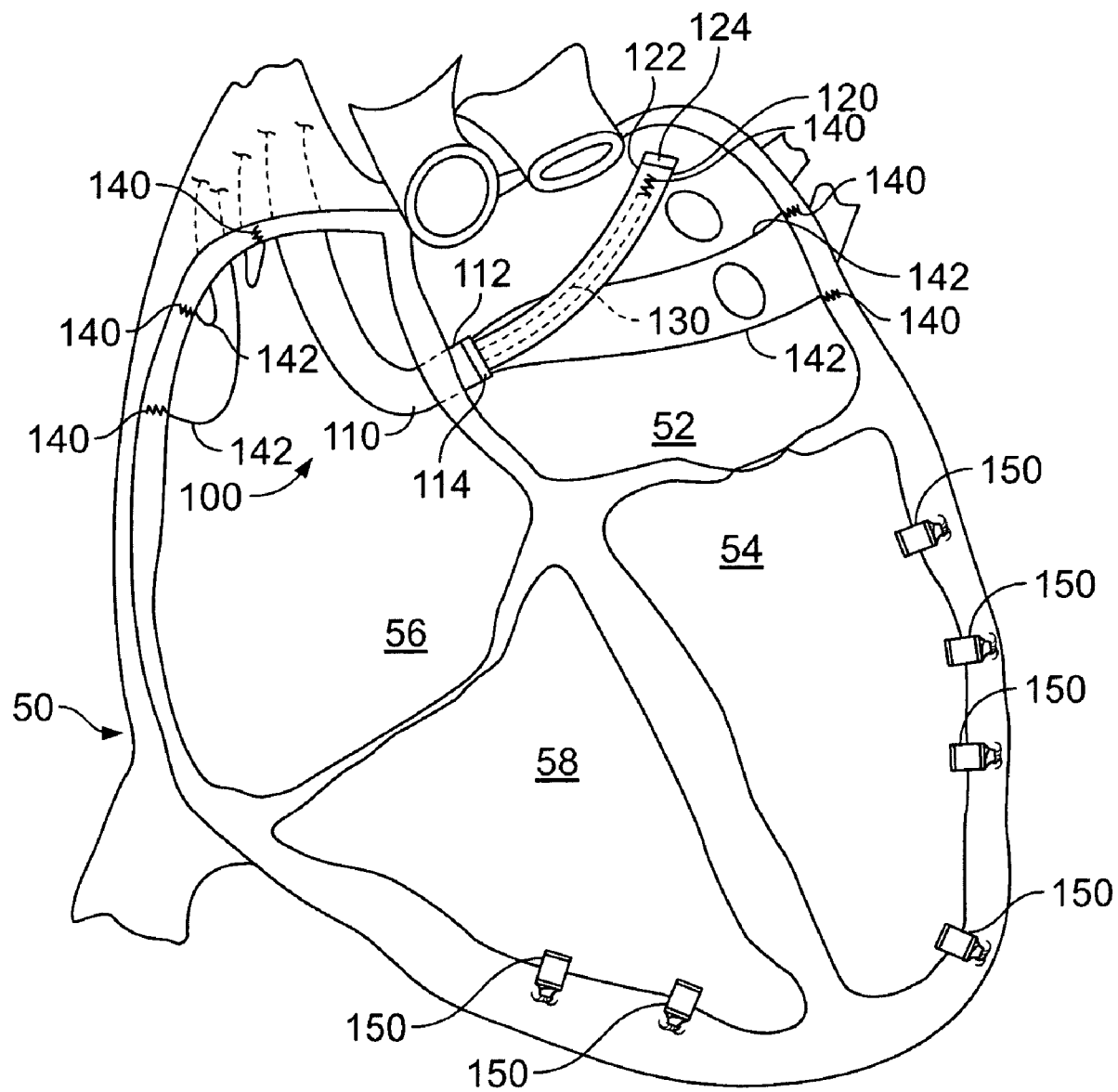
FIG. 2 is a perspective view of the electrodes of FIG. 1 in a plurality of heart chambers.

Referring to FIGS. 1-2, an electrode delivery system 100 may include a guide sheath device 110 and an inner sheath device 120 that is movable within a lumen of the guide sheath device 110. The distal portion 112 of the guide sheath device 110 may be directed through the venous system to the targeted heart chamber (e.g., the left atrium 52 in the depicted embodiment). The inner sheath device 120 may be used to direct an individual wired electrode 140 to an inner wall of any of the heart chambers 52, 54, 56, or 58 of a patient 10, as described in more detail below. The guide sheath device 110 may provide access to one or more of the heart chambers 52, 54, 56, 58 for the inner sheath device 120 and for a plurality of the wired electrodes 140. For example, three wired electrodes 140 are shown in FIGS. 1-2 in the left atrium 52, and three wired electrodes 140 are shown in FIGS. 1-2 in the right atrium 56. As described in more detail below, the inner sheath device 120 may be directed through the guide sheath 110 adjacent to the wires 142 from electrodes 140 that were previously passed through the inside of the same or a similar inner sheath 120. Optionally, the guide sheath 110 may also be used to deliver one or more wireless electrode assemblies 150 to one or more of the heart chambers 52, 54, 56, 58. For example, four wireless electrode assemblies 150 are shown in FIGS. 1-2 in the left ventricle 54, and two wireless electrode assemblies 150 are shown in FIGS. 1-2 in the right ventricle 58.

The wired electrodes 140 may be inserted into the inner wall of one or more heart chambers 52, 54, 56, 58. In the embodiment depicted in FIG. 1, the wired electrodes 140 are implanted through the inner wall of the left atrium 52 and the right atrium 56, and the wireless electrode assemblies 150 are implanted through the inner wall of the left ventricle 54 and right ventricle 58. In other embodiments, the wired electrodes 140 may be delivered to the inner wall of one, two, three, or four of the heart chambers 52, 54, 56, 58 using the electrode delivery system 100. In these circumstances, the wireless electrode assemblies 150 may not be used in a particular patient, or optionally, the wireless electrode assemblies 150 may be delivered to the inner wall of one or more heart chambers 52, 54, 56, 58 to supplement or coordinate with electrical stimulation provided by the wired electrodes 140. For example, in some embodiments, the wired electrodes 140 may be secured to the heart tissue in the left atrium 52, the left ventricle 54, the right atrium 56, and the right ventricle 58 while the wireless electrode assemblies are not implemented. Alternatively, in some embodiments, the wired electrodes 140 may be secured to the heart tissue in the left atrium 52, the right atrium 56, and the right ventricle 58 while the wireless electrode assemblies are secured to the inner wall of the left ventricle 54 and the right ventricle 58.

Still referring to FIGS. 1-2, the wired electrodes 140 may include a wire and a fixation device, such as a helical tine, to secure the electrode 140 to the heart chamber wall. In some embodiments, the wired electrode 140 may comprise a wired pacing lead that delivers electrical pulses to the heart tissue from the distal end thereof. After the electrode delivery system 100 delivers the electrodes 140 to the selected areas of the heart chamber walls, the wire for each of the wired electrodes 140 may be connected to an electrical device, such as an implantable pulse generator 160. For example, the wires may extend from the fixation device of the electrodes 140 in the heart chamber walls, through the superior vena cava and the venous system, and to a sub-clavicle region of the patient's body 10 for connection with the pulse generator 160. The pulse generator 160 may provide electrical stimulation to heart tissue near the distal portion of the electrodes 140 (e.g., at the fixation device) to cause the heart to contract and hence pump blood. The pulse generator 160 may include a power supply source (e.g., a battery device or the like), control circuitry, and at least one electrical pulse generating circuitry so that electrical pulses can be delivered through the wire 142 to the fixation device 144 of electrode 140.

Referring to FIG. 2, the guide sheath device 110 of the electrode delivery system 100 may include a distal portion 112 that is configured to be delivered into one or more heart chambers 52, 54, 56, 58 of a patient 10. For example, the guide sheath device 110 may be steerable so that the distal portion 112 can be inserted through an incision in a patient's skin, into the venous system, and through the superior vena cava toward the right atrium 56. In some embodiments, the guide sheath device 110 may include push wires, pull wires, or shape memory devices to permit a user to manipulate the distal portion of the guide sheath device 110 through the venous system. In certain embodiments, the guide sheath device 110 may include a marker band 114 at its distal end to permit viewability of the distal end of the guide sheath device 110 using medical imaging techniques. Such a marker band 114 may aid a physician when steering the guide sheath device 110 to the targeted heart chamber 52, 54, 56, or 58. In some embodiments, the distal portion 112 of the guide sheath device 110 can be directed through the superior vena cava, through the right atrium, through the atrial septum (e.g., through the fossa ovalis), and into left atrium 52. Such transeptal access provides an opportunity to secure wired electrodes 140 or wireless electrode assemblies 150 to the left atrium 52, the left ventricle 54, or both. It should be understood that the guide sheath device 110 may access the heart chambers 52, 54, 56, and 58 using other paths, such as through the tricuspid valve and into the right ventricle or through the femoral artery and descending aorta and into the left ventricle.

The guide sheath device 110 may include at least one lumen passing from a proximal portion (not shown in FIG. 2) to the distal portion 112. As such, a user may access the heart chamber by passing a device (e.g., the inner sheath device 120, the deployment device 130, the wired electrode 140, or the like) longitudinally through the lumen from the proximal portion (e.g., outside the patient's body 10) and out through the distal end of the guide sheath device 110. The guide sheath device 110 may comprise a biocompatible polymer material and, in some circumstances, may have steerable curves along the distal portion 112 or may have a fixed curved shape along the distal portion 112. As described in more detail below, the lumen of the guide sheath device 110 may have a lateral width that is sufficient to permit the passage of the inner sheath device 120 in a side-by-side configuration with one or more wires 142 from previously secured electrodes 140. Such a configuration may permit a plurality of wired electrodes 140 to be passed through a single lumen (e.g., guide sheath device 110) and secured to the inner wall of at least one heart chamber (e.g., the left atrium 52), thereby creating multiple electrical stimulation sites. Further, the outer sheath device 110 may permit a plurality of wired electrodes 140 or wireless electrode assemblies 150 to be delivered to the left heart chambers 52 and 54 without requiring multiple crossings of the fossa ovalis. This may be useful in cases where crossing the atrial septum with a delivery device for each of the wired electrodes 140 or wireless electrode assemblies 150 to be delivered to the left chambers may be contraindicated, depending upon the condition of the patient.

Still referring to FIG. 2, the system 100 may also include the inner sheath device 120 that is movable through a lumen of the guide sheath device 110 so that a distal portion 122 that may be inserted into one or more heart chambers 52, 54, 56, 58. The inner sheath device 120 may exit the lumen of the guide sheath device 110 at the distal end and then may be directed to a targeted location on the inner wall of the heart chamber (e.g., the left atrium 52 is depicted in FIG. 2). As described in more detail below, the inner sheath device 120 may be used to direct a deployment device 130 to the tissue surface so as to secure a wired electrode 140 to an inner wall of the heart chamber. In such embodiments, the inner sheath device 120 and the deployment device 130 may be withdrawn while the guide sheath device 110 remains in the patient's heart 50 or elsewhere in the patient's venous system. Then, a second wired electrode 140 may be delivered with the same or a similar inner sheath device 120 through the lumen of the guide sheath device 110. In these circumstances, the wires 142 of the electrodes 140 that were previously delivered inside the inner sheath device 120 may be disposed in the guide sheath device 110 side by side with the inner sheath device 120. Accordingly, the inner sheath device 120 may be navigated in the one or more heart chambers 52, 54, 56, 58 without substantial restriction from the wires 142 of the previously implanted electrodes 140.

The inner sheath device 120 may include at least one lumen passing from a proximal portion (not shown in FIG. 2) to the distal portion 122. As such, a user may pass the deployment device 130 longitudinally through the lumen and to the distal portion 122 near the heart tissue at the inner wall of the heart chamber. The inner sheath device 120 may comprise a biocompatible polymer material and, in some circumstances, may have steerable curves along the distal portion 122 or may have a fixed curve shape along the distal portion 122. For example, the inner sheath device 120 may have a fixed curve shape along the distal portion 122 appropriate to the anatomy of the heart wall being targeted. In some embodiments, the inner sheath device 120 may include push wires, pull wires, or shape memory devices to permit a user to manipulate the distal portion 122. In some embodiments, the inner sheath device 120 may include a marker band 124 at its distal end to permit viewability of the distal end of the inner sheath device 120 using medical imaging techniques. Such a marker band 124 may aid a physician when steering the inner sheath device 120 to the targeted site along the heart chamber wall.

The electrode delivery system 100 may be used to secure a plurality of wired electrodes 140 and/or wireless electrode assemblies 150 to the inner wall of one or more chambers of the heart 50. In the implant configuration depicted in FIG. 2, a plurality of wired electrodes 140 are secured to the inner walls of the right atrium 56 and the left atrium 52, and a plurality of wireless electrode assemblies 150 are secured to the inner walls of the right ventricle 58 and the left ventricle 54. Alternatively, no wireless electrode assemblies 150 may be used, and the guide sheath device 110 may access each targeted chamber of the heart 50 so that a plurality of wired electrodes 140 may be secured to the walls of those heart chambers. Thus, in some implementations, the wired electrodes 140 may be secured to the inner wall of the left atrium 52, left ventricle 54, right atrium 56, right ventricle 58, or a combination thereof. In such circumstances, the guide sheath device 110 may be directed to a different heart chamber immediately after a first heart chamber is completed (e.g., after all of the wired electrodes 140 for the first heart chamber have been secured). Alternatively, the user may elect to withdraw the guide sheath device 110 from the patient's body 10 after each heart chamber is completed (e.g., after all of the wired electrodes 140 for that particular heart chamber have been secured), and then redirect the guide sheath device 110 to a different heart chamber. This process permits the guide sheath device 110 to direct a second set of wired electrodes 140 to the different heart chamber without navigational restriction from the wires of the previously implanted electrodes 140. After all of the wired electrodes 140 have been secured in the targeted heart chambers, both the guide sheath device 110 and the inner sheath device 120 may be withdrawn to expose the proximal ends of the wires 142. Then, the proximal ends of the wires 142 could be connected to an implantable pulse generator 160 (FIG. 1) or to an external pulse generator outside the patient's body.

The pulse generator 160 or other electrical devices in communication with the wired electrodes 140, the wireless electrodes 150, or both may cause the wired electrodes 140 and the wireless electrodes 150 to coordinate with one another to provide controlled pacing stimulation at multiple pacing sites. In some embodiments in which no wireless electrode assemblies 150 are used and the wired electrodes 140 are secured to the inner wall of the left atrium 52, left ventricle 54, right atrium 56, right ventricle 58, or a combination thereof, the pulse generator 160 may transmit electrical pulses via the wires 142 to the fixation devices of wired electrodes 140 to provide controlled pacing stimulation at multiple electrode sites. In some embodiments in which the wired electrodes 140, the wireless electrodes 150, or both are used for defibrillation therapy, the creation of multiple electrode sites in one or more heart chambers may substantially reduce the total electrical energy required to perform defibrillation therapy.

Such a reduction in the total electrical energy may be achieved because the electric fields fall off rapidly with distance away from the site of stimulation. For example, to capture the entire heart, some conventional defibrillators must use large input energy to capture tissue far removed from the stimulating electrodes. In some embodiments described herein, one wired electrode 140 or wireless electrode 150 may capture a tissue volume of about 10 cubic centimeters centered on that electrode, with a low energy pacing pulse. In these circumstances, about twenty electrodes 140 or 150 could therefore capture the entire left ventricle, where ventricle fibrillation can arise. It is believed that delivery of approximately 100 times the pacing threshold energy to each of the twenty electrodes 140 or 150 would require less than one milli-joule of input energy, a small fraction of the total electrical energy delivered by conventional defibrillators. In addition, multi-site defibrillation energy could be delivered to the multiple electrodes 140 or 150 in a timed sequence that optimizes the probability of defibrillation. Such a sequence may be determined by analysis of the local ECG signals measured from each electrode 140 or 150 during a defibrillation episode. Furthermore, the electrodes 140 or 150 may be employed to repress premature electrical stimulations arising in the myocardium that can precipitate fibrillation events. These "hot spots" can be repressed by rapid stimulation with a local electrode 140 or 150 to keep such tissue refractory. It should be understood that, in other embodiments, the electrodes 140 or 150 implanted in the heart tissue may provide multi-site pacing that is initiated on detection of a premature beat to ensure continued synchronization of the tissues.

There are many heart conditions that can benefit from pacing at multiple sites in the heart chamber walls. For example, congestive heart failure patients may benefit from bi-ventricular pacing, that is, pacing of both the left ventricle 54 and the right ventricle 58 in a timed relationship. In another example, pacing at multiple sites may be beneficial where heart tissue through which electrical energy must propagate is scarred or dysfunctional, which condition halts or alters the propagation of an electrical signal through that heart tissue. In these circumstances, multiple-site pacing inside the heart chambers 52, 54, 56, 58 may be useful to restart the propagation of the electrical signal immediately downstream or adjacent of the dead or sick tissue area. In a further example, synchronized pacing at multiple sites in the heart chambers 52, 54, 56, 58 may inhibit the onset of fibrillation resulting from slow or aberrant conduction, thereby reducing the need for or usage of cardiac defibrillators. In another example, pacing at a sufficient number of sites in one or more heart chambers, for example in the left atrium 52 and right atrium 56, may force all tissue to depolarize in a synchronous manner to prevent the arrhythmias or atrial fibrillation.

Still referring to FIG. 2, the wireless electrode assemblies 150 may operate as described in pending application Ser. No. 10/971,550 (filed on Oct. 20, 2004), Ser. No. 11/075,375 (filed on Mar. 7, 2005), and Ser. No. 11/075,376 (filed on Mar. 7, 2005), all owned by the assignee of this application, which describe various features of wireless electrode assemblies, systems to deliver the wireless electrode assemblies to the heart, and electronic components to activate the wireless electrode assemblies to deliver electrical stimulation. Some of these features may be applicable to particular embodiments of the wireless electrode assemblies 150 described herein, so these three patent applications (Ser. Nos. 10/971,550, 11/075,375, and 11/075,376) are incorporated herein by reference. As described below in connection with FIG. 8, the wireless electrode assemblies 150 may include a handle member 156 that is configured to be detachably retained by the deployment device 130 of the electrode delivery system 100.

In some embodiments, each of the wireless electrode assemblies 150 may have an internal coil that is inductively coupled with an external power source coil to charge an electrical charge storage device (e.g., a battery or capacitor) contained within the wireless electrode assembly 150. In those embodiments in which the wireless electrode assemblies 120 include a rechargeable battery, the battery may provide power for delivering pacing energy to the heart tissue, and for operating communications, logic, and memory circuitry contained within the assembly, as described in pending application Ser. Nos. 10/971,550, 11/075,375, and 11/075,376. In alternative embodiments, one or more of the wireless electrode assemblies 150 may have no energy storage device, such as a battery or capacitor. In such circumstances, the wireless electrode assembly 150 may be comprised, for example, of a ferrite core having caps at each end with ring electrodes encircling the caps. A number of turns of fine insulated wire may be wrapped around the central portion of the core so as to receive energy from a magnetic field produced by a shaped driving signal and designed to activate the electrodes.

In certain embodiments of the wireless electrode assemblies 150, a transmitter and the antenna device 159 (FIG. 1) may serve to recharge the batteries within the electrode assemblies, as described in previously incorporated application Ser. Nos. 10/971,550, 11/075,375, and 11/075,376. Such a transmitter and antenna device 159 may be implanted into the patient's body 10 (e.g., incorporated into a rib-mounted device as shown in FIG. 1 or incorporated into the pulse generator 160), incorporated into furniture, incorporated into the patient's bed, or worn by the patient (e.g., in a vest-type garment).

Referring to FIGS. 3A-E, some embodiments of the electrode delivery system 100 may include a deployment device 130 that is detachably coupled to the wired electrode 140. The deployment device 130 may be used to direct the wired electrode 140 to heart tissue 55 along the inner wall of a heart chamber 52, 54, 56, or 58. The deployment device 130 may be used to apply a penetration force or torque to the wired electrode 140 so that at least a portion of the wired electrode 140 passes through the inner surface of the heart chamber wall (e.g., through endocardium tissue and possibly into myocardium tissue). After the wired electrode 140 is secured to the heart wall tissue, the deployment device 130 may detach from the wired electrode 140 so that the inner sheath device 120 and the deployment device 130 can be withdrawn through the lumen of the guide sheath device 110 (FIG. 2). In some embodiments, the deployment device 130 may be preassembled with a corresponding wired electrode 140. In such circumstances, a separate deployment device 130 may be directed through guide sheath device 110 (and through the inner sheath device 120) for each wired electrode 140 that will be implanted in the heart chamber.

Figure 3A:
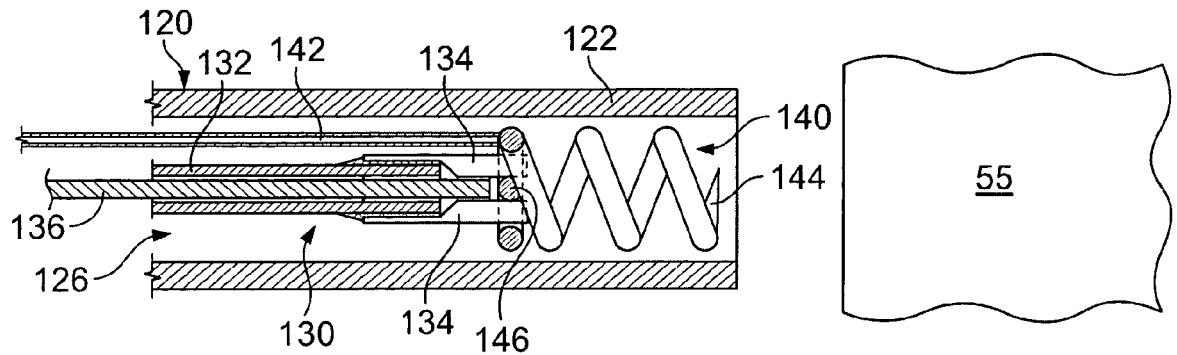
FIGS. 3A-E are partial cross-section views of a portion of an electrode delivery system, in accordance with some embodiments described herein.

Referring to FIG. 3A, as previously described, the distal portion 122 of the inner sheath device 120 may be delivered to the heart chamber 52, 54, 56, or 58 via a lumen in the guide sheath device 110. As such, a user may direct the distal end of the inner sheath device 120 toward the heart wall tissue 55, and the deployment device 130 may pass through a lumen 126 of the inner sheath device 120 so that the fixation device 144 of the wired electrode 140, such as a helical tine or the like, approaches the heart wall tissue 55. In some embodiments, the deployment device 130 may include an elongated body 132 having one or more attachment members 134 disposed at a distal end thereof. In this embodiment, the attachment members 134 comprise two opposing fingers that are configured to grasp a handle member 146 of the wired electrode 140. In such circumstances, if the elongated body is moved axially in a distal or proximal direction, the fixation device 144 of the wired electrode 140 may also move in that direction. Further, if a twisting torque is applied to the elongated body 132, the opposing fingers 134 may apply a torque to the wired electrode 140, as described in more detail below. The deployment device 130 may also comprise an actuation member, such as a push rod 136 (refer also to FIG. 5) or a pull wire (refer to FIG. 6), that may be adjusted by a user to detach the wired electrode 140 from the opposing fingers 134.

Figure 3B:
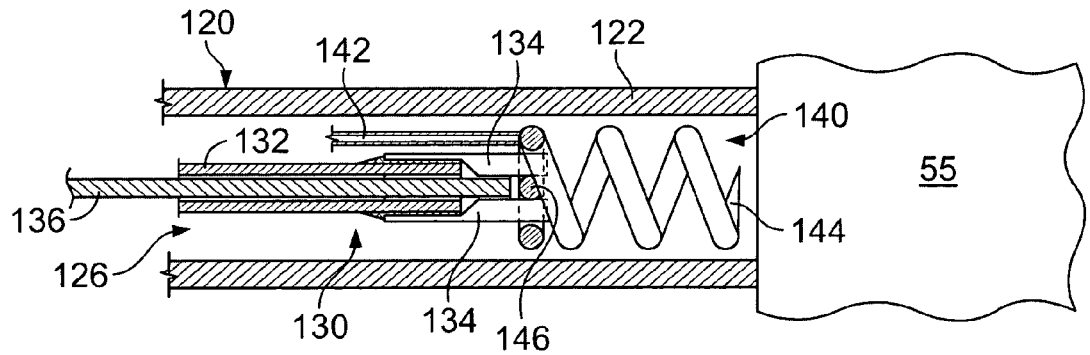

Referring to FIG. 3B, the distal portion 122 of the inner sheath device 120 may be directed to a position adjacent the heart wall tissue 55. In such circumstances, the deployment device 130 may direct the fixation device 144 of the wired electrode 140 to abut the heart wall tissue 55. For example, a user may move the elongated body 132 axially in a distal direction so that the fixation device 144 is forced against the heart wall tissue 55. Alternatively, the deployment device 130 may move contemporaneously with the inner sheath device 120 so that forcing the distal end of the inner sheath device 120 against the heart wall tissue 55 causes the fixation device 144 to also be forced against the heart wall tissue 55.

Figure 3C:
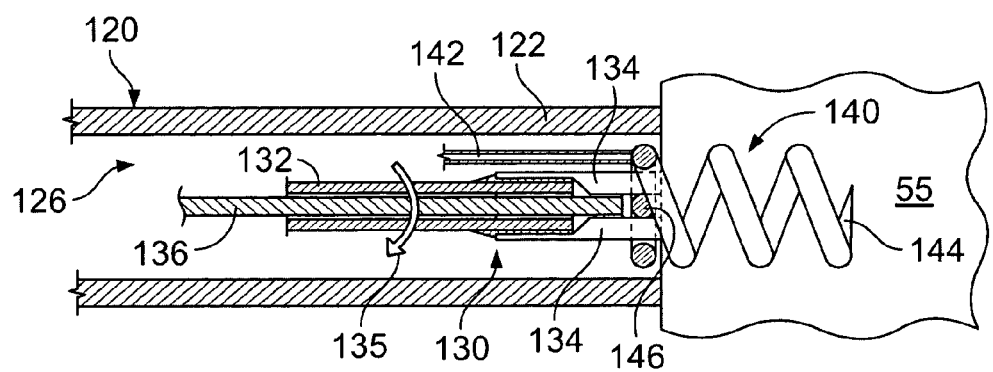

Referring to FIG. 3C, the deployment device 130 may transmit a penetration force, a penetration torque, or a combination thereof to the wired electrode 140 so that the fixation device 144 passes through the inner surface of the heart chamber wall 55 (e.g., through endocardium tissue and, in some embodiments, into myocardium tissue). In the embodiments depicted in FIG. 3C, a user may apply a twisting force 135 to the elongated body 132 (e.g., twisting the proximal portion of the elongated body of outside the patient's body 10) so that the opposing fingers 134 apply a penetration torque to the fixation device 144 of the wired electrode 140. Such a penetration torque may cause the fixation device 144 to screw into the heart wall tissue 55. The wire 142 of the wired electrode 140 may extend out through the proximal end of the inner sheath 120 (not shown in FIG. 3C) so that temporary electrical stimulation or testing may be performed. For example, when the fixation device 144 is deployed into the heart tissue 55, the user may perform temporary pacing tests through the wire 142 to verify that the wired electrode 140 has been positioned in a suitable location. In another example, the user may perform temporary electrocardiogram testing at the implantation site before permanently detaching the deployment device 130. In such circumstances, the fixation device 144 may serve as a first electrode and the distal end of the inner sheath device 122 may include a second electrode (e.g., connected by an integrated conductor trace along the body of the inner sheath device 120) so that a bipolar electrocardiogram may be performed.

Figure 3D:
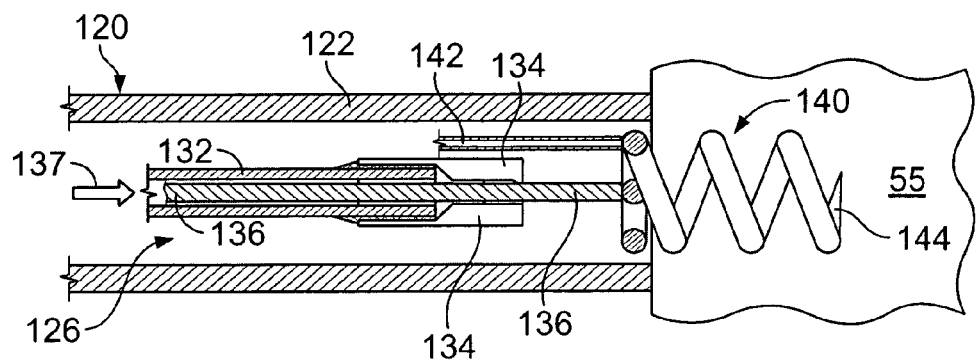

Referring now to FIG. 3D, the deployment device 130 may be detached from the wired electrode 140 after the wired electrode has been secured at a suitable site in the heart tissue 55. As previously described, the deployment device 130 may include an actuation member, such as a push rod 136 or a pull wire (refer to FIG. 6), that may be adjusted by a user to detach the wired electrode 140 from the opposing fingers 134. In this embodiment, the actuation member is a push rod 136 that is axially movable relative to the elongated body 132 of the deployment device 130. The distal end of the push rod 136 may be configured to press against the handle member 146 of the wired electrode 140 so that an axial force 137 applied from the push rod on the handle member 146 pushes the handle member 146 from the fingers 134. As described in more detail below, other embodiments of the actuation member 136 may also include a pull wire mechanism to release the wired electrode 140 from the deployment device 130.

Figure 3E:
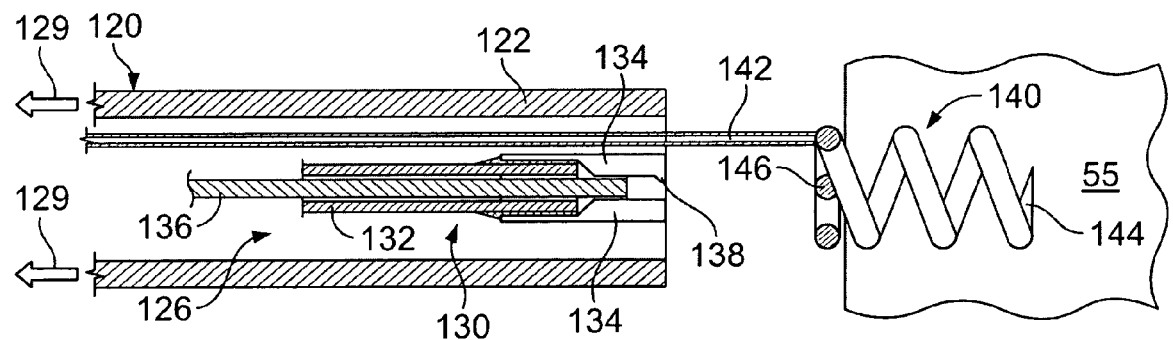

Referring to FIG. 3E, after the deployment device 130 is detached from the wired electrode 140, the deployment device 130 and the inner sheath 120 may be withdrawn from the implantation site in the heart tissue 55. A withdrawing force 129 may be applied to the inner sheath device 120 and the deployment device 130 so that both are withdrawn through the lumen of the guide sheath device 110 (FIG. 1) while the guide sheath device 110 remains in the heart chamber. If the deployment device 130 is coupled to the inner sheath device 120 (e.g., so that the deployment device 130 is not fully removable from the lumen 126 of the inner sheath device 120), the user may pull on the proximal portion of the inner sheath device 120 to withdraw both the inner sheath device 120 and the deployment device 130. Otherwise, the user may pull on the deployment device 130 before or at the same time as the inner sheath device 120. As shown in FIG. 3E, the actuation member 136 may be returned to its previous position so that, if desired, the deployment mechanism 130 may approach the fixation device 144 to reattach with the wired electrode 140 (e.g., to remove the wired electrode 140, to further secure the wired electrode 140 to the tissue 55, or to reposition the wired electrode 140 at another site). Accordingly, a user may operate the deployment device 130 to adjust or remove the fixation device 144 that has been implanted in the heart wall tissue 55. In some embodiments, at least one of the opposing fingers 134 may have a ridge 138 that facilitates the grasping action when attached to the handle member 146 of the wired electrode.

Referring to FIGS. 4A-B, the distal portion 112 of the guide sheath device 110 (FIG. 1) may remain inside the heart chamber 52, 54, 56, 58 (FIG. 1) so that a second wired electrode 140*d*, which may be detachably coupled to the same or similar deployment device 130 inside the same or similar inner sheath device 120, can be directed to a second implantation site 55*d* in the hearth tissue 55. In such circumstances, a wire 142*c* of a previously deployed wired electrode 140*c* that was once inside the inner sheath device 120 (refer to FIG. 4A) may be disposed side by side with inner sheath device 120 inside the guide sheath device 110 (refer to FIG. 4B) while a second wired electrode 140*d* is being implanted. Such a configuration permits the distal portion 122 of the inner sheath device 120 to be navigated to the second implantation site without substantial restriction from the wires 142a, 142b, and 142c of the previously implanted electrodes (e.g., implanted electrode 140c). Further, such a configuration permits a plurality of wired electrodes 140a (refer to wire 142a), 140b (refer to wire 142b), 140c, and 140d to be delivered into a heart chamber through an individual guide sheath device 110 without repeatedly moving the guide sheath device 110.

As shown in FIG. 4A, the deployment device 130 and the inner sheath 120 may be withdrawn from the implantation site 55c in the heart tissue 55 after the deployment device 130 is detached from the wired electrode 140c (described, for example, in connection with FIGS. 3C-E). The withdrawing force 129 may be applied to the inner sheath device 120 and the deployment device 130 so that both are withdrawn through the lumen 116 of the guide sheath device 110. If the deployment device 130 is coupled to the inner sheath device 120 (e.g., so that the deployment device 130 is not fully removable from the lumen 126 of the inner sheath device 120), the user may pull on the proximal portion of the inner sheath device 120 to withdraw both the inner sheath device 120 and the deployment device 130. As the inner sheath device 120 is being withdrawn, the wire 142c of the recently implanted wired electrode 140c is disposed inside the lumen 126 of the inner sheath device 120 while wires 140a and 140b of previously implanted wired electrodes (not shown in FIG. 4A) are disposed adjacent to the inner sheath device 120 inside the lumen 116 of the guide sheath device 110. The inner sheath device 120 and the deployment device 130 may be fully removed from the proximal portion of the guide sheath device 110 (e.g. outside the patient's body 10) so that the wire 142c of the recently implanted electrode 144c is not inside the inner sheath device 120.

Referring to FIG. 4B, the same inner sheath device 120 (or a new inner sheath device having the same construction) may be directed through the lumen 116 of the guide sheath device 110 to the inner wall of the heart chamber 52, 54, 56, or 58 (FIG. 1). In this implementation, the inner sheath device is passed through the guide sheath device 110 so that the wire 142c of the recently implanted electrode 140c is not inside the lumen 126 of the inner sheath device 120, but is instead disposed adjacent to the inner sheath device 120 inside the guide sheath device 110. As such, when the distal portion 122 of the inner sheath device 120 is directed out through the distal end of the guide sheath device 110 inside the heart chamber, the inner sheath's distal portion 122 may be navigated to a second implantation site 55d without substantial restriction from the wire 140c that was previously inside the lumen 126 of the inner sheath device 120 (as shown in FIG. 4A). Accordingly, the lumen 116 of the guide sheath device 110 may have a lateral width that is sufficient to permit the passage of the inner sheath device 120 in a side-by-side configuration with one or more wires 142 from previously implanted electrodes 140. For example, the outer sheath device 110 may have an outer diameter that is less than about 0.20 inches and may be about 0.170 inches, and the outer sheath device 110 may have an inner diameter of less than about 0.13 inches and may be about 0.110 inches. In these embodiments, the inner sheath device 120 may have an outer diameter of less than about 0.12 inches and may be about 0.096 inches, and the inner sheath device 120 may have an inner diameter of less than about 0.10 inches and may be about 0.078 inches. It should be understood that the outer sheath device 110 and inner sheath device 120 may other dimensions to permit the passage of the inner sheath device 120 in a side-by-side configuration with one or more wires 142 from previously implanted electrodes 140.

A second wired electrode 140d may be preassembled with a corresponding deployment device 130, which has a construction similar to the previously withdrawn deployment device 130 depicted in FIG. 4A. Thus, the second wired electrode 140d may be directed through the inner sheath device 120 toward the targeted heart chamber. In an alternative embodiment, the second wired electrode 140d may be preassembled with a corresponding deployment device 130 and may be passed through a new inner sheath device 120, both of which have a similar construction as the previously withdrawn deployment device 130 and the inner sheath device 120 depicted in FIG. 4A. In such circumstances, each wired electrode 140c or 140d may be packaged with its own inner sheath device 120, its own deployment device 130, or both, and the user may discard the previously used inner sheath device 120 and deployment device 130 each time a subsequent wired electrode 140d is to be delivered through the guide sheath device 110. It should be understood, that in some alternative embodiments, the second wired electrode 140d may be detachably coupled to the previously used deployment device 130 and disposed inside the same inner sheath device 120 that was previously employed during the implantation of the other wired electrode 140c (refer to FIG. 4A). In such circumstances, the user may attach the handle member 146d of the second wired electrode 140d to the deployment device 130 just as the previously implanted electrode 140c was attached thereto.

Still referring to FIG. 4B, the second wired electrode 140d may be directed through the lumen 126 toward the second implantation site 55d while the wires 142a, 142b, and 142c of the previously implanted wired electrodes (e.g., wired electrode 140c) are not disposed in the lumen 126. For example, the user may apply an axial force 139 upon the deployment device 130 so that the wired electrode 140 is advanced toward the second implantation site 55d. The fixation device 144d of the second wired electrode 140d may be directed to a position in abutment with the heart tissue 55 at the second implantation site 55d. As previously described in connection with FIGS. 3A-E, the second wired electrode 140d may be secured to the heart tissue 55 at the second implantation site 55d.

Figure 5:
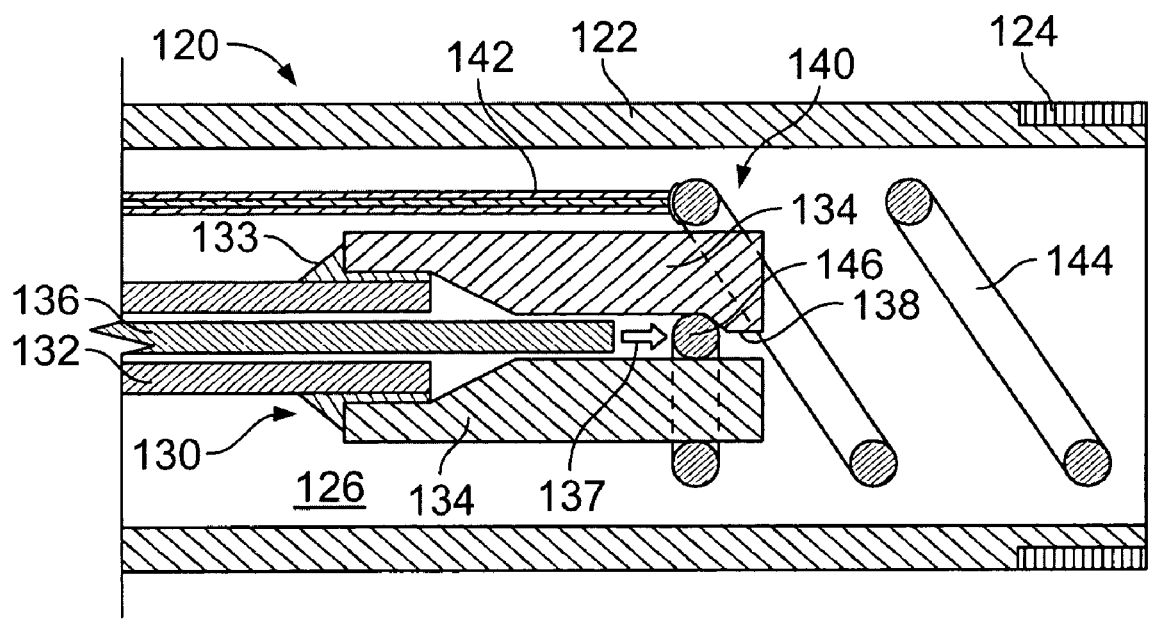
FIG. 5 is a partial cross-section view of a portion of an electrode delivery system, in accordance with some embodiments described herein.
Figure 6:
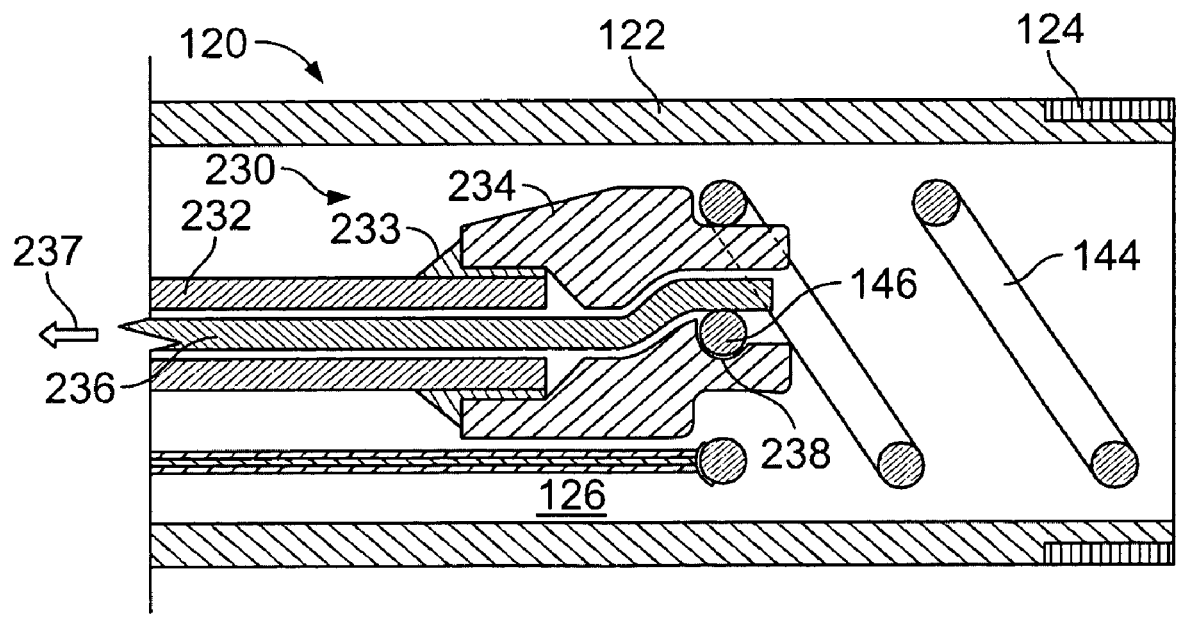
FIG. 6 is a partial cross-section view of a portion of an electrode delivery system, in accordance with some embodiments described herein.

Referring now to FIGS. 5-6, the deployment device 130 or 230 may detach from the wired electrode 140 using an actuation member, such as a push rod or a pull wire, that can be controlled by a user at the proximal end of the deployment device 130 or 230 (e.g., outside the patient's body. As shown in FIG. 5, some embodiments of the deployment device 130 may include the elongated body 132 having one or more attachment members 134 disposed at a distal end thereof. A seal member 133, such as a biocompatible polymer, may be disposed between the elongated body 132 and the attachment members 134. As previously described in connection with FIGS. 3A-E, the attachment members 134 may include opposing fingers that are configured to grasp the handle member 146 of the wired electrode 140 so that the fixation device 144 of the wired electrode 140 may be moved in an axial direction or twisted when the user controls the elongated body 132. Also in this embodiment, the deployment device 130 includes a push rod actuation member 136 that may be adjusted by a user to detach the wired electrode 140 from the opposing fingers 134. For example, the distal portion of the push rod 136 may be axially movable relative to the elongated body 132 of the deployment device 130 so that the distal end of the push rod 136 presses against the handle member 146. In some embodiments, push rod 136 may comprise a shape memory material (e.g., nitinol or the like) so that the distal portion of the push rod 136 may be axially adjusted by electrically charging or discharging the push rod 136. In other embodiments, the distal portion of the push rod 136 may be adjusted by the actuation of a plunger device at the proximal portion of the deployment device 130. In these various circumstances, an axial force 137 applied from the push rod 136 on the handle member 146 may cause the opposing fingers 134 to slide away from the handle member 146.

Referring to FIG. 6, some embodiments of a deployment device 230 may include a pull wire actuation member 236 that may be adjusted to detach the deployment device 230 from the wired electrode 240. In this embodiment, the deployment device 230 includes an elongated body 232 having an attachment member 234 disposed at a distal end thereof. A seal member 233, such as a biocompatible polymer, may be disposed between the elongated body 232 and the attachment member 234. The attachment member 234 may include an adapter that is configured to pinch the handle member 146 of the wired electrode 140 when the pull wire 236 is adjacent the handle member 146. In such circumstances, the fixation device 144 of the wired electrode 140 may be moved in an axial direction or twisted when the user controls the elongated body 232. The pull wire actuation member 236 may be adjusted by a user to detach the wired electrode 140 from the adapter 234. For example, the distal portion of the pull wire 236 may be axially movable relative to the elongated body 232 (e.g., via an axial force 237) so that the distal end of the pull wire 236 slides away from the handle member 146. In some embodiments, pull wire 236 may comprise a shape memory material (e.g., nitinol or the like) so that the distal portion of the pull wire 236 may be axially adjusted by electrically charging or discharging the pull wire 236. In other embodiments, the distal portion of the pull wire 236 may be adjusted by the pulling a plunger device at the proximal portion of the deployment device 230. In these various circumstances, movement 237 the distal portion of pull wire 236 releases the handle member 146 from the channel 238 in the adapter 234, thereby detaching the wired electrode 140 from the deployment device 230. Thus, the deployment device 230 may be used to deliver and secure the wired electrode 140 to the heart tissue 55 as described in connection with FIGS. 3A-E.

Figure 7A:
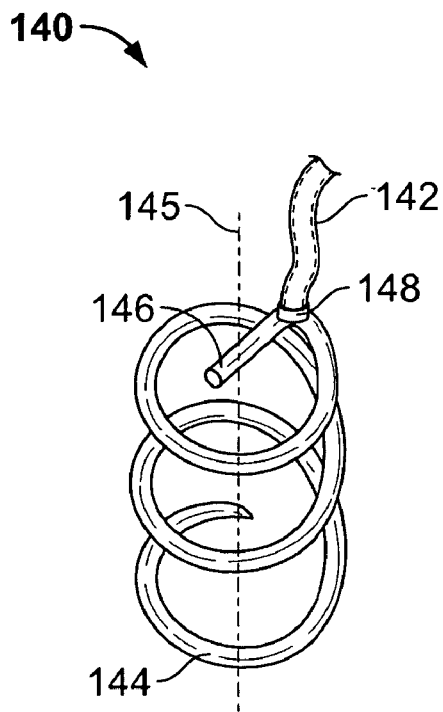
FIGS. 7A-B are perspective views of wired electrodes in accordance with some embodiments described herein.

Referring to FIG. 7A, some embodiments of the wired electrode 140 may comprise an insulated wire 142 that is coupled with a fixation device 144. For example, the wire 142 may join the fixation device 144 at a brazed joint 148 so as to permit the transmission of electrical pulses from the wire 142 to the fixation device 144. As shown in FIG. 7A, the wire 142 may be coupled to the fixation device 144 so that the wire 142 is laterally offset from a longitudinal axis 145 of the fixation device 144. The wire 142 may comprise a conductive metallic material that is insulated with a substantially nonconductive material. In some embodiments, the wire 142 may have fine width to reduce the likelihood of a clot or thrombus forming along the wire during the contractions of the heart 50. For example, the wire 142 may have an outside diameter of less than about 0.010 inches and may be about 0.007 inches, where the diameter of the conductive metallic material is less than about 0.008 inches and may be about 0.005 inches.

In these embodiments in which the wire 142 is a fine width, the risk of forming a clot or thrombus (especially in the left atrium or left ventricle) may be reduced. In some circumstances, the wire 142 may be coated with an anticoagulant to further reduce the risk of forming a clot or thrombus along the wire. It is believed that the fine width or the wire 142 facilitates the process of embedding the wires in the heart tissue along the heart chamber wall. For example, after the fixation device 144 has been implanted, the wire 142 may be rested against the heart chamber wall where the heart tissue will grow over a substantially portion of the wire 142 over a period of time in which the patient heals. In some embodiments, the outer surface of the wire 142 may be textured or porous to facilitate the embedding process. While this embedding process is occurring, some patients may be provided with an anticoagulant treatment to reduce the likelihood of forming a clot or thrombus. In some circumstances in which the risk of forming a clot or thrombus in a particular heart chamber is substantially high, the wireless electrode assemblies 150 may be employed in place of the wired electrodes 140 to prevent the formation of a clot or thrombus along the wire 142.

The fixation device 144 may comprise a conductive material so that electrical stimulation may be delivered through the fixation device 144 when the fixation device 144 is proximate to heart tissue 55. Also, the fixation device 144 may comprise a radiopaque material to permit viewability of the wired electrode implantation using medical imaging techniques. In some embodiments, the fixation device may comprise stainless steel, platinum, gold, iridium oxide, titanium oxide or a combination thereof. For example, the fixation device may comprise a platinum iridium alloy or may comprise a gold plated stainless steel material. As previously described, some embodiments of the fixation device 144 may include a helical tine. In this embodiment, the helical tine extends around the longitudinal axis 145. Alternatively, the fixation device 144 may comprises one or more shafts, one or more barbs, one or more curly tines, or a combination thereof, as described, for example, in previously incorporated application Ser. Nos. 10/971,550, 11/075,375, and 11/075,376. In some embodiments, the fixation device 144 may have a longitudinal length that is sufficient to penetrate into the inner wall of the heart chamber and to secure into the heart tissue 55. For example, the fixation device 144 having a helical tine configuration may have a length of less than 0.125 inches and may have a length of about 0.112 inches, where the spacing between one or more of the coils is about 0.040 inches. Also in some embodiments, the fixation device 144 may have a lateral width that is suitable to pass through the inner sheath device 120. For example, the fixation device 144 having the helical tine configuration may have an outside diameter of less than 0.080 inches and may be about 0.065 inches, where the tine material has a diameter of less than about 0.020 inches and may be about 0.012 inches. The fixation device 144 may include a handle member 146 that is configured to be detachably retained by the deployment device 130 or 230, as previously described in connection with FIGS. 5-6. In the embodiments in which the fixation device 144 includes a helical tine configuration, the handle member 146 may include a cross bar portion that is integrally formed with the helical tine.

Still referring to FIG. 7A, the fixation device 144 may serve as a unipolar electrode when secured to the heart tissue 55 (FIGS. 3A-E). In such implementations, the complementary electrode may be disposed in or near the heart 50 to form an electrical stimulation circuit in which electrical pulses are transmitted through at least a portion of the heart tissue 55. For example, the pulse generator 160 (FIG. 1) implanted in the patient's body 10 may serve as the opposing electrode (e.g., the anode) for one or more of the fixation devices 144 (e.g., the cathodes) that are secured in the heart chamber wall. In another example, a neighboring fixation device 144 may be controlled by the pulse generator 160 so that the first fixation device 144 and the neighboring fixation device 144 serves as opposing electrodes.

Figure 7B:
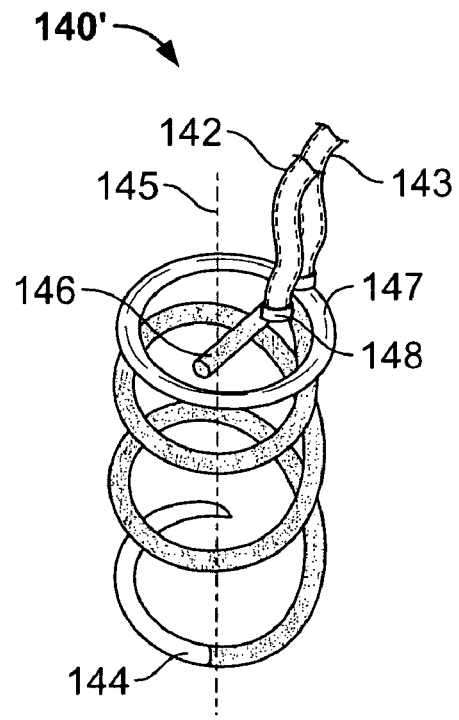

Referring to FIG. 7B, some embodiments of the wired electrodes 140' may serve as bipolar electrodes. For example, the wired electrode 140' may comprise two wires 142 and 143 having a fine width as previously described. The wires 142 and 143 may be separately insulated to each have an outside diameter of less than about 0.010 inches (preferably about 0.007 inches). Alternatively, the wires 142 and 143 may share an outer insulation covers so that the outside diameter is less than about 0.020 inches, less than about 0.015 inches, and preferable about 0.013 inches. As previously described, the wires 142 and 143 may be coated with an anticoagulant to further reduce the risk of forming a clot or thrombus along the wire and the outer surfaces of the wires 142 and 143 may be textured or porous to facilitate the embedding process. The wires 142 and 143 are insulated from one another so that the first wire 142 is electrically connected to the fixation device 144 and the second wire 143 is electrically connected to a second electrode 147, such as a ring electrode 147 disposed at a non-tip portion of the fixation device 144. The fixation device 144 may be insulated except at the tip portion. As such, the tip portion of the fixation device 144 and the ring electrode 147 at the rear portion of the fixation device 144 may serve as opposing electrodes to provide bipolar electrical stimulation.

Figure 8:
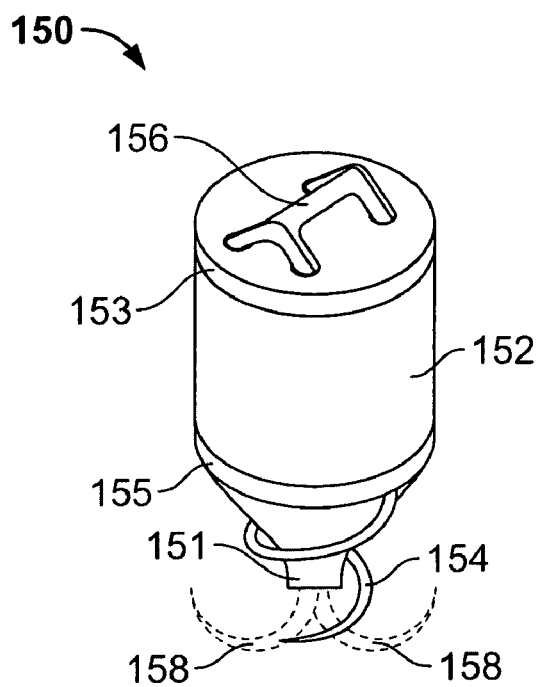
FIG. 8 is a is a perspective view of a wireless electrode assembly in accordance with some embodiments described herein.

Referring to now FIG. 8, the wireless electrode assemblies 150 may include a handle member 156 that is configured to be detachably retained by the deployment device 130 or 230, as previously described in connection with FIGS. 5-6. The handle member 156 may comprise a shaft portion that is secured to a rear portion of the wireless electrode body 152. As such, the handle member 156 of the wireless electrode assembly 150 may operate with the deployment device 130 or 230 in a manner similar to handle member 146 of the wired electrode 140 (refer to FIGS. 3A-E and 5-6). As described in pending application Ser. Nos. 10/971,550, 11/075,375, and 11/075,376 (which were previously incorporated by reference), the wireless electrode assembly 150 includes a main body 152 that, in this example, is cylindrically shaped with a tip portion 151 at a distal end. The wireless electrode assembly 150 may include two bipolar electrodes 153 and 155 that are capable of discharging an electrical pulse. Electrode 155 is located at the distal end of the body 152, and the other electrode 153 is located at a proximal end of the body 152. In this embodiment, the tip portion 151 of the body 152 has a modified cone shape that facilitates delivery of the distal end of the electrode assembly 150 into heart tissue. A fixation device 154, such as a helical tine, may extend from the tip portion 151 so that the wireless electrode assembly may be secured to the heart tissue. In some embodiments, the wireless electrode assembly 150 may include adjustable tines 158 that can be deployed from the tip portion 151 to reduce the likelihood of the assembly unscrewing from the heart tissue. As previously described in connection with FIGS. 1-2, the wireless electrode assemblies 150 may be implanted in one or more heart chambers 52, 54, 56, 58 to supplement or operate in coordination with the wired electrodes 140 that are secured to the heart chamber walls.

It should be understood that the wired electrodes 140 and wireless electrode assemblies 150 described herein may be delivered to portions of the heart 50 other than the inner walls of the heart chambers 52, 54, 56, and 58. For example, the wired electrodes 140, wireless electrode assemblies 150, or both may be delivered to the exterior of the heart 50 using a minimally invasive catheter approach. In such circumstances, an outer catheter may be inserted into the pericardial space using a sub-xiphoid approach or a right atrial approach. A deployment device 130 or 230 may be passed through the outer catheter so that a wired electrode 140 or a wireless electrode assembly 150 is delivered to the exterior surface of one or more heart chambers. As previously described, the deployment device may apply a penetration force, a penetration torque, or both to secure the fixation device 144 or 154 (e.g., a helical tine or the like) to the heart tissue (e.g., to the myocardium from the exterior surface of the heart 50). In these embodiments, the wired electrodes 140 or wireless electrode assemblies may be employed to control any heart rhythm disturbance or to provide defibrillation.

A number of embodiments of the invention have been described. Nevertheless, it will be understood that various modifications may be made without departing from the spirit and scope of the invention. Accordingly, other embodiments are within the scope of the following claims.

What is claimed is:

1. A system, comprising:
a cardiac stimulation wired electrode assembly, comprising:
    a fixation device configured to be driven in a direction of a longitudinal axis of the fixation device to securely implant the fixation device into an interior wall of a heart chamber, the fixation device comprising a conductive helical coil member having a piercing tip at a distal end and an integrally formed cross bar extending inward at a proximal end of the coil member toward the center of the coil member to form a handle; and
    at least one insulated wire including a first end that is attached directly to the conductive material of the fixation device at an attachment point that is laterally offset from the longitudinal axis of the fixation device, and including a second end that is connectable to an implantable pulse generator device; and
wherein the fixation device handle is confined within a lateral profile of the fixation device, the handle member configured to be releasably retained by a deployment device at a first location, and wherein the insulated wire is laterally offset from the deployment device and the first location when the handle member is releasably retained by the deployment device at the first location.

2. The system of claim 1, wherein the insulated wire includes an outside diameter of less than about 0.010 inches.

3. The system of claim 2, wherein the insulated wire has an outside diameter of about 0.007 inches.

4. The system of claim 3, wherein the insulated wire is coated with an anticoagulant.

5. The system of claim 1, wherein the fixation device comprises a helical tine that extends around the longitudinal axis.

6. The system of claim 1, wherein the insulated wire is connectable to the implantable pulse generator device so that electrical pulses are deliverable through the fixation device and to at least a portion of the heart chamber wall.

7. The system of claim 1, wherein the fixation device comprises a radiopaque material configured to permit viewability of at least a portion of the fixation device using a medical imaging technique.

8. The system of claim 1, wherein the fixation device comprises at least one of a platinum-iridium alloy or a gold-plated stainless steel material.

9. The system of claim 1, comprising:
a guide sheath device including a distal end and a guide conduit extending therethrough;
an inner sheath device including a distal end configured to pass through the guide conduit and including an inner conduit extending therethrough;
a deployment device configured to direct at least the wired electrode assembly through the inner conduit into a heart chamber; and
wherein the inner sheath device has a lateral width smaller than the guide conduit such that the inner sheath device is configured to slide through the guide conduit and configured to direct a second wired electrode assembly toward a second tissue site in the heart chamber while a first insulated wire is located in the guide conduit laterally outside the inner sheath device, the first insulated wire attached to a previously delivered first wired electrode assembly.

10. The system of claim 9, wherein the deployment device includes an elongate body, a distal end, and a detachment mechanism at the distal end configured to detachably couple with at least one of the first or second wired electrode assemblies.

11. The system of claim 10, wherein the detachment mechanism at the distal end is configured to detachably couple with a respective first or second handle member included as a portion the first or second wired electrode assemblies.

12. The system of claim 9, wherein the deployment device is configured to transmit a rotational force to the wired electrode assembly.

13. The system of claim 9, wherein the deployment device is configured to direct at least a portion of the first or second electrode assemblies to penetrate through an endocardium and into a myocardium.

14. The system of claim 13, wherein the deployment device is configured to direct a respective first or second helical tine included as a portion of a first or second electrode assembly through the endocardium and into the myocardium.

15. The system of claim 9, wherein the inner sheath is configured to maintain a longitudinal axis of at least one of the first or second wired electrode assemblies in an orientation substantially perpendicular to a plane defined by the heart chamber wall at a respective first or second tissue site.

* * * * *